United States Patent [19]

Kranz et al.

[11] Patent Number: 4,470,842
[45] Date of Patent: Sep. 11, 1984

[54] HERBICIDALLY ACTIVE NOVEL 3-ALKEN(IN)YL-MERCAPTO(AMINO)-4-AMINO-6-TERT-BUTYL-1,2,4-TRIAZIN-5-ONES

[75] Inventors: Eckart Kranz, Wuppertal; Kurt Findeisen, Odenthal; Ludwig Eue, Leverkusen; Robert Schmidt, Bergisch-Gladbach, all of Fed. Rep. of Germany

[73] Assignee: Bayer Aktiengesellschaft, Leverkusen, Fed. Rep. of Germany

[21] Appl. No.: 454,898

[22] Filed: Dec. 30, 1982

[30] Foreign Application Priority Data

Jan. 15, 1982 [DE] Fed. Rep. of Germany ....... 3201110

[51] Int. Cl.³ .................... C07D 253/6; A01N 43/64
[52] U.S. Cl. ........................................ 71/93; 544/182
[58] Field of Search ............................ 544/182; 71/93

[56] References Cited

U.S. PATENT DOCUMENTS 3,671,523 6/1972 Westphal et al. ................... 544/182
4,386,953 6/1983 Kranz et al. ........................ 544/182

FOREIGN PATENT DOCUMENTS 49416 4/1982 European Pat. Off. .

Primary Examiner—John M. Ford
Attorney, Agent, or Firm—Sprung, Horn, Kramer & Woods

[57] ABSTRACT

3-Alkenylmercapto-, 3-alkinylmercapto-, 3-alkenylamino- and 3-alkinylamino-4-amino-6-tert.-butyl-1,2,4-triazin-5-ones of the general formula

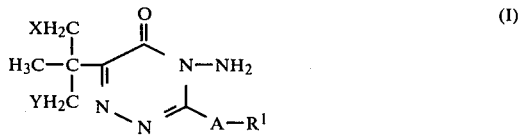

in which
A represents a sulphur or a radical of the general formula —NR²—,
R² represents a hydrogen atom or an alkyl group,
R¹ represents an alkenyl or alkinyl group,
X represents a halogen atom or an alkoxy group, and
Y represents a hydrogen or halogen atom or an alkoxy group, are new, are prepared as described, and find use as herbicides.

10 Claims, No Drawings

HERBICIDALLY ACTIVE NOVEL 3-ALKEN(IN)YL-MERCAPTO(AMINO)-4-AMINO-6-TERT-BUTYL-1,2,4-TRIAZIN-5-ONES

The present invention relates to certain new 3-alkenylmercapto-, 3-alkinylmercapto-, 3-alkenylamino- and 3-alkinylamino-4-amino-6-tert.-butyl-1,2,4-triazin-5-ones, to processes for their production, and to their use as herbicides, in particular as selective herbicides.

It has already been disclosed that substituted 1,2,4-triazin-5-ones, such as, for example, 4-amino-3-methylmercapto-6-tert.-butyl-1,2,4-triazin-5-one, can be used as herbicides (see, for example, German Patent Specification No. 1,795,784 and U.S. Patent Specification No. 3,671,523). In certain crops, however, selective use of the previously known triazinones is not possible since damage may also occur to certain crop plants, owing to the high herbicidal power of all members of this group of substances; accordingly, the previously known triazinones are not sufficiently tolerated by various crop plants.

The present invention now provides, as new compounds, the 3-alken(in)yl-mercapto(amino)-4-amino-6-tert.-butyl-1,2,4-triazin-5-ones of the general formula

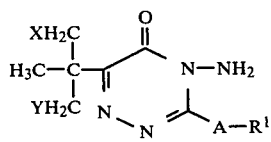 (I)

in which
A represents sulphur or a radical of the general formula —NR²—,
R² represents a hydrogen atom or an alkyl group,
R¹ represents an alkenyl or alkinyl group,
X represents a halogen atom or an alkoxy group and
Y represents a hydrogen or halogen atom or an alkoxy group.

The present invention further relates to a process for the production of a compound of the present invention, characterized in that (a) a 4-amino-3-mercapto-6-tert.-butyl-1,2,4-triazin-5-one of the formula

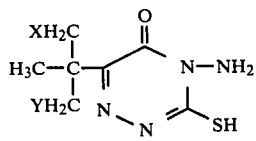 (II)

in which
X and Y have the meanings given above, is reacted with a halide of the general formula Hal—R¹ (III)

in which
R¹ has the meaning given above, and
Hal represents a halogen atom, in the presence of a base and, if appropriate, in the presence of a diluent, or (b) a 3-alkylmercapto-4-amino-6-tert.-butyl-1,2,4-triazin-5-one of the general formula

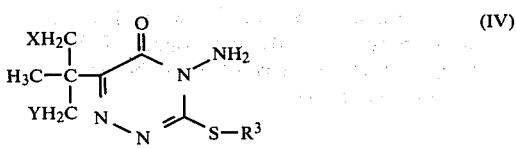 (IV)

in which
X and Y have the meaning given above, and
R³ represents an alkyl group, is reacted with an amine of the general formula

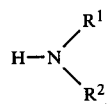 (V)

in which
R¹ and R² have the meanings given above, in the presence of a diluent and, if appropriate, in the presence of a lower aliphatic carboxylic acid.

In addition, it has been found that the 3-alken(in)yl-mercapto(amino)-4-amino-6-tert.-butyl-1,2,4-triazin-5-ones of the formula (I) possess good herbicidal properties, in particular selective herbicidal properties.

Compared to the known 4-amino-3-methylmercapto-6-tert.-butyl-1,2,4-triazin-5-one, which is a similar compound chemically and in terms of its action, the compounds according to the invention surprisingly exhibit substantially better toleration by important crop plants, such as, in particular, wheat, oats and corn coupled with an equally good general herbicidal action. The active compounds according to the invention thus represent a substantial enrichment of herbicidal means, in particular of the selective chemical combating of weeds.

Preferred compounds according to the present invention are those in which
A represents sulphur or a radical of the general formula —NR²—,
wherein
R² represents a hydrogen atom or a straight-chain or branched alkyl group having 1 to 4 carbon atoms;
R¹ represents a straight-chain or branched alkenyl group having 3 to 6 carbon atoms or a straight-chain or branched alkinyl group having 3 to 6 carbon atoms;
X represents a fluorine, chlorine or bromine atom or a straight-chain or branched alkoxy group having 1 to 4 carbon atoms; and
Y represents a hydrogen, fluorine, chlorine or bromine atom, or a straight-chain or branched alkoxy group having 1 to 4 carbon atoms.

Particularly preferred compounds of the present invention are those in which
A represents sulphur or a radical of the general formula —NR²—, wherein
R² represents a hydrogen atom or a methyl or ethyl group;
R¹ represents a radical selected from —CH₂—CH=CH₂, —CH₂—CH=CH—CH₃, —CH₂—C(CH₃)=CH₂, —CH(CH₃)—CH=CH₂, —C(CH₃)₂—CH=CH₂, —CH₂C|CH, —CH(CH₃)—C|CH and —C(CH₃)₂—C|CH;
X represents a fluorine or chlorine atom or a methoxy, ethoxy or isopropoxy group; and
Y represents a hydrogen, fluorine or chlorine atom or a methoxy, ethoxy or isopropoxy group.

If, for example, 4-amino-6-chloro-tert.-butyl-3-mercapto-1,2,4-triazin-5-one and propargyl bromide are used as starting materials, the course of the reaction according to reaction variant (a) may be represented by the following equation:

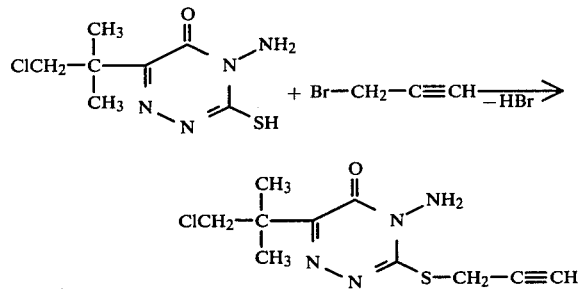

If, for example, 4-amino-6-fluoro-tert.-butyl-3-methylthio-1,2,4-triazin-5-one and allylamine are used as starting materials, the course of the reaction according to reaction variant (b) may be represented by the following equation:

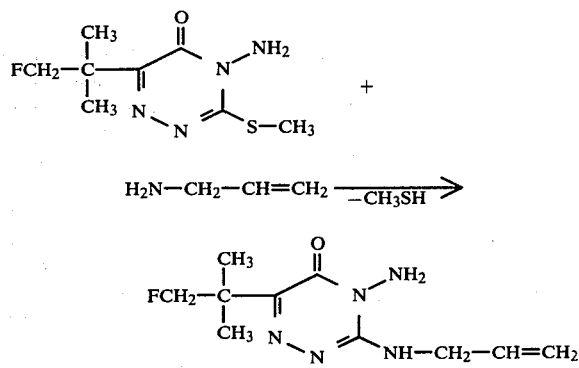

Preferred 4-amino-3-mercapto-6-tert.-butyl-1,2,4-triazin-5-ones of formula (II) to be used as starting materials for reaction variant (a) are those in which X and Y represent the radicals which have already been mentioned for these substituents in connection with the desciption of the preferred and particularly preferred compounds according to the invention.

The 4-amino-3-mercapto-6-tert.-butyl-1,2,4-triazin-5-ones of the formula (II) are not yet known; however, they form the subject of United States patent applications Ser. Nos. 299,919, filed Sept. 8, 1981, now U.S. Pat. Nos. 4,386,953 and 411,745, filed Aug. 26, 1982, now pending. They are obtained when, in a first stage, a pivaloyl cyanide of the general formula

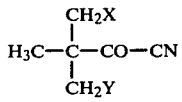  (VI)

in which

X and Y have the meanings given above, ($\alpha$) is reacted with an inorganic acid (such as hydrohalic acid) at a temperature between 0° and 40° C., if appropriate in the presence of a liquid carboxylic acid (such as acetic acid) as the solvent, or ($\beta$) is added onto a carbonium ion which is formed from an olefin (such as isobutylene) or a tertiary alcohol (such as tert.-butanol) and a strong acid (such as sulphuric acid) and the subjected to hydrolysis; and the resulting trimethylpyruvic acid amide of the general formula

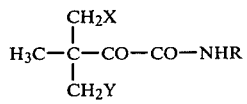  (VIIa)

in which

X and Y have the meanings given above, and

R represents a hydrogen atom (obtainable according to variant ($\alpha$), or an alkyl group, especially a tert.-butyl group, (obtainable according to variant ($\beta$), is reacted in a second stage, in a manner which is in itself known, either directly in the solution obtained or after intermediate isolation, if appropriate after prior hydrolysis to the free, substituted trimethylpyruvic acid of the general formula

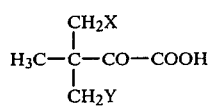  (VIIb)

in which

X and Y have the meanings given above, with a thiocarbohydrazide of the formula

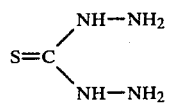  (VIII)

in aqueous or in aqueous-acidic solution (such as a solution containing a hydrohalic acid), if appropriate in the presence of an organic solvent (such as, in particular, dimethylformamide) at a temperature between 0° and 100° C.

The pivaloyl cyanides of the formula (VI) are not yet known. They, also form the subject of our above-mentioned patent applications. The pivaloyl cyanides of the formula (VI) can be obtained by reacting the corresponding pivaloyl halides or pivaloyl anhydrides of the formulae IXa and IXb, respectively,

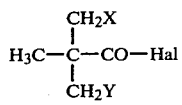  (IXa)

and

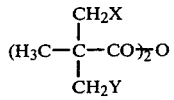  (IXb)

in which

X and Y have the meanings given above, and

Hal represents a halogen atom, preferably a chlorine or bromine atom, with trimethylsilyl cyanide, if appropriate in the presence of an inert organic solvent (such as acetonitrile) at a temperature between 80° and 110° C. The trimethylsilyl cyanide, (CH$_3$)$_3$Si-CN, is known (see, for example, Synthesis 1979, pages 522 and 523).

The pivaloyl halides and pivaloyl anhydrides of the formulae (IXa) and (IXb) are known, or can be prepared by known processes:

Preferred halides of formula (III) additionally to be used as starting materials for reaction variant (a) are those in which $R^1$ represents the radicals which have already been mentioned for this substituent in connection with the preferred and particularly preferred compound according to the invention and Hal represents a chlorine or bromine atom.

The halides of the formula (III) are generally known compounds of organic chemistry.

Preferred 3-alkylmercapto-4-amino-6-tert.-butyl-1,2,4-triazin-5-ones of formula (IV) to be used as starting materials for reaction variant (b) are those in which X and Y represent the radicals which have already been mentioned in these substituents in connection with the description of the preferred and particularly preferred compounds according to the invention, and $R^3$ represents an alkyl group having 1 to 4 carbon atoms, such as, especially, a methyl group.

The 3-alkylmercapto-4-amino-6-tert.-butyl-1,2,4-triazin-5-ones of the formula (IV) are not yet known. They, also, form the subject of the above-mentioned patent applications, and are obtained by reacting a 4-amino-3-mercapto-6-tert.-butyl-1,2,4-triazin-5-one of the formula (II) with an alkyl halide (such as methyl iodide or methyl bromide) according to reaction variant (a).

Preferred amines of formula (V) additionally to be used as starting materials for reaction variant (b) are those in which $R^1$ and $R^2$ represent the radicals which have already been mentioned for these substituents in connection with the description of the preferred and particularly preferred compounds according to the invention.

The amines of the formula (V) are generally known compounds of organic chemistry.

Suitable diluents for reaction variant (a) according to the present invention are protic and aprotic solvents. These include, for example, water, alcohols, carboxylic acids, acetone, acetonitrile, dimethylformamide, dimethylsulphoxide and toluene.

The reaction variant (a) according to the invention is carried out in the presence of a base. These include any of the organic and, especially, inorganic bases which can customarily be used (such as sodium hydroxide, potassium hydroxide, sodium carbonate and potassium carbonate).

In carrying out reaction variant (a) according to the invention, the reaction temperatures can be varied within a relatively wide range. In general, the reaction is carried out at a temperature between 0° and 120° C., preferably between 20° and 100° C.

In carrying out the process according to the invention, 1 to 2 mols of the halide of the formula (III) are preferably employed per mol of the compound of the formula (II). The end products are isolated in a generally customary manner.

According to a preferred embodiment of reaction variant (a) according to the invention, the reaction is carried out in a two-phase system (for example, aqueous sodium hydroxide solution or potassium hydroxide solution/toluene or methylene chloride) with the addition of 0.01–1 mol of a phase transfer catalyst (such as an ammonium compound or phosphonium compound) per mol of the compound of formula (II).

Suitable diluents for reaction variant (b) according to the invention are any of the inert organic solvents. These include hydrocarbons (such as toluene and xylene), chlorinated aromiatic hydrocarbons (such as chlorobenzene, 1,2-dichlorobenzene and 1,2,4-trichlorobenzene), ethers (such as tetrahydrofuran and dioxane), alcohols (such as methanol, ethanol, propanol and isopropanol), amides (such as N,N-dimethylformamide and tetramethylurea) or sulphoxides (such as dimethylsulphoxide). Isopropanol is preferably used for the reaction.

In carrying out reaction variant (b) according to the invention, the reaction temperatures can be varied within a relatively wide range. In general, the reaction is carried out at a temperature between 60° and 90° C.

The reaction according to reaction variant (b) can be carried out under atmospheric pressure as well as under elevated pressures.

A particularly advantageous embodiment of reaction variant (b) comprises carrying out the reaction in the presence of at least an equimolar amount of a $C_1$ to $C_6$ aliphatic carboxylic acid. Acetic acid is preferably used for this purpose. This process permits the use of a relatively small excess of amine. In this embodiment, the reaction rate can be increased by the addition of a catalytic amount of an organic sulphonic acid. p-Toluenesulphonic acid is preferably used for this purpose.

In carrying out reaction variant (b) according to the invention, 1 to 2 mols of a lower aliphatic carboxylic acid, 0.01 to 0.05 mol of an organic sulphonic acid and 1 to 5 mols of the amine of the formula (V) are advantageously employed per mol of the 3-alkylmercaptotriazinone of the formula (IV), and the mixture is heated until the splitting off of the mercaptan is complete, and is then worked up.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In addition to showing a very good general herbicidal action, the active compounds according to the invention are well tolerated by crop plants. Thus, it is possible selectively to combat important graminaceous weeds in important crop plants, for example, in wheat, oats and corn.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

When used as herbicides, the active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.1 and 10 kg/ha, preferably between 0.2 and 6 kg/ha.

The present invention also provides herbicidal compositions containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The examples which follows serve to illustrate the invention further.

PREPARATIVE EXAMPLES

EXAMPLE 1

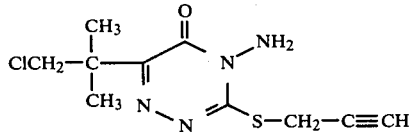
(1)

(Reaction variant (a))

18.6 g (80% stength solution in toluene=0.125 mol) of propargyl bromide and 0.5 g of pentyltributylphosphonium bromide were added to a solution of 23.5 g (0.1 mol) of 4-amino-6-chloro-tert.-butyl-3-mercapto-1,2,4-triazin-5-one and 4.4 g of sodium hydroxide in 40 ml of water. The reaction mixture was stirred for about 20 hours at room temperature, 100 ml of toluene were then added, and the mixture was filtered. The filtrate was washed with 100 ml of water, with 100 ml of 1 N sodium hydroxide solution and again with water. The organic phase was dried over sodium sulphate, filtered and concentrated. The oily residue was brought to crystallization by trituration in diisopropyl ether, and the product was recrystallized from ethyl acetate/petroleum ether. 13.8 g (57.5% of theory) of 4-amino-6-chloro-tert.-butyl-3-propargylthio-1,2,4-triazin-5-one of melting point 107°-108° C. were obtained.

Preparation of the starting material

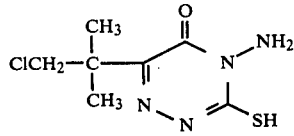

2.31 kg (15.88 mols) of chloropivaloyl cyanide were added to 9 liters of a solution of hydrogen bromide in glacial acetic acid (33% strength) at room temperature, while stirring. The mixture was stirred for a further 4 hours at room temperature. Thereafter, 288 ml (15.88 mols) of water were added at 7° to 10° C. (exothermic reaction, approximately 37° C.), and the mixture was stirred for a further 3 hours at room temperature. The reaction solution was thereafter introduced into a mixture of 2.03 kg of thiocarbohydrazide and 15.9 liters of 1 N hydrochloric acid at 7° to 10° C. (strongly exothermic reaction). This reaction mixture was stirred further for 2 hours at 7° to 10° C. and for 14 hours at room temperature. Thereafter, the precipitated crystals were filtered off, washed with water and dried. 2,995 g (80.4% of theory) of crude 4-amino-6-chloro-tert.-butyl-3-mercapto-1,2,4-triazin-5-one of melting ponit 202° to 208° C. were obtained.

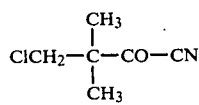

8,300 g (49.5 mols) of 92.5% strength β-chloropivaloyl chloride were warmed to 100° C., and 4,950 g (50 mols) of trimethylsilyl cyanide were added in the course of about 2 hours. The trimethylsilyl chloride formed was distilled off simultaneously. After the end of the addition, the temperature was slowly increased to 140° C., and the mixture was stirred for about 1.5 hours at this temperature. The reaction mixture was then distilled in vacuo. 7,500 g of β-chloropivaloyl cyanide of boiling point 62°-65° C./16 mbar were obtained.

EXAMPLE 2

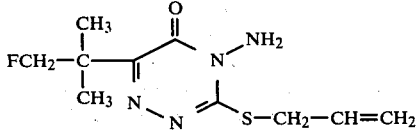
(2)

(Reaction variant (a))

26.6 g (0.22 mol) of allyl bromide were added to a solution of 43.6 g (0.2 mol) of 4-amino-6-fluoro-tert.-butyl-3-mercapto-1,2,4-triazin-5-one in 200 ml of 1 N sodium hydroxide solution at room temperature. The reaction mixture was stirred for approximately 20 hours at room temperature, the organic phase was then taken up in chloroform, and the solution was washed with three times 150 ml of 0.1 N sodium hydroxide solution, dried over sodium sulphate, filtered and concentrated. The oily residue was degassed at 50° C./0.05 mbar, and recrystallized from ethyl acetate/petroleum ether. 20.8 g (40% of theory) of 3-allylthio-4-amino-6-fluoro-tert.-butyl-1,2,4-triazin-5-one of melting point 75° to 74° C. were obtained.

EXAMPLE 3

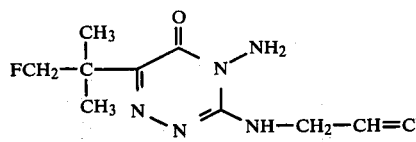
(3)

(Reaction variant (b))

11.06 g (0.05 mol) of 4-amino-6-fluoro-tert.-butyl-3-methylthio-1,2,4-triazin-5-one and 14.3 g (0.25 mol) of allylamine were added to 6 g (0.1 mol) of glacial acetic acid in 250 ml of isopropanol, and the mixture was stirred while cooling with ice. Thereafter, the reaction mixture was heated under reflux for about 40 hours. The mixture was allowed to cool, and concentrated, the residue was taken up in methylene chloride, and the solution was washed with 200 ml of 1 N sodium hydroxide solution and with 200 ml of water, dried over sodium sulphate, filtered and concentrated. The oily residue was crystallized by trituration with diisopropyl ether. After recrystallization from ethyl acetate/petroleum ether, 4.9 g (41% of theory) of 3-allylamino-4-amino-6-fluoro-tert.-butyl-1,2,4-triazin-5-one of melting point 100°-104° C. where obtained.

Preparation of the starting material

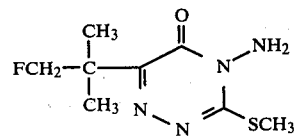

Using fluoropivaloyl cyanide as a starting material crude 4-amino-6-fluoro-tert.-butyl-3-mercapto-1,2,4-triazin-5-one was first obtained, in a yield of 80%, by the method described in Example 1. 3,347.4 g (12 mols)

of the 4-amino-6-fluoro-tert.-butyl-3-mercapto-1,2,4-triazin-5-one obtained in this manner were dissolved in 15 liters of 1 N sodium hydroxide solution. After the product had completely dissolved, 1,873.6 g of methyl iodide were added dropwise at 7° to 10° C. After the end of the addition, the mixture was stirred further for 2 hours at 7° to 10° and overnight at room temperature. Thereafter, the solid obtained was filtered off under suction, washed with water and dried. 2,285 g (65% of theory) of 4-amino-6-fluoro-tert.-butyl-3-methylthio-1,2,4-triazin-5-one of melting point 121–122° C. were obtained.

The compounds of the general formula

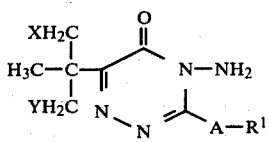 (I)

which are listed in Table 1 below were obtained in an analogous manner and according to the processes according to the invention:

| Example No. | X | Y | A | R¹ | Melting point (°C.) or $n_D^{20}$ |
|---|---|---|---|---|---|
| 4 | F | H | S | —CH$_2$—CH=CH—CH$_3$ | 1.566 |
| 5 | F | H | S | —CH$_2$—C≡CH | 94–95 |
| 6 | Cl | H | S | —CH$_2$—CH=CH$_2$ | 65–66 |
| 7 | Cl | H | S | —CH$_2$—CH=CH—CH$_3$ | 1.577 |
| 8 | Cl | H | NH | —CH$_2$—CH=CH$_2$ | 82–85 |
| 9 | F | F | S | —CH$_2$—CH=CH—CH$_3$ | 1.555 |
| 10 | Cl | H | NH | —CH$_2$—C≡CH | 116–17 |
| 11 | F | H | NH | —CH$_2$—C≡CH | 129–31 |
| 12 | F | H | N(CH$_3$) | —CH$_2$—C≡CH | viscous oil |
| 13 | F | H | S | —CH$_2$—CH=CH$_2$ | 1.550 |
| 14 | F | H | S | —CH$_2$—C≡CH | 68–69 |
| 15 | Cl | H | N(CH$_3$) | —CH$_2$—C≡CH | 1.562 |
| 16 | F | F | NH | —CH$_2$—CH=CH$_2$ | 101–102 |
| 17 | H$_5$C$_2$O— | H | S | —CH$_2$—C≡CH | 69–70 |
| 18 | H$_3$CO— | H | S | —CH$_2$—C≡CH | 133–34 |
| 19 | H$_5$C$_2$O— | H | S | —CH$_2$—CH=CH$_2$ | 54–56 |
| 20 | H$_5$C$_2$O— | H | NH | —CH$_2$—CH=CH$_2$ | 1.536 |
| 21 | H$_5$C$_2$O— | H | S | —CH$_2$—CH=CH—CH$_3$ | 1.557 |

The herbicidal activity of the compounds of this invention is illustrated by the following biotest examples.

In these examples the compounds according to the present invention are each identified by the number (given in brackets) of the corresponding preparative example.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction

In this test the compounds (1), (3), (5) and (8), for example, showed a very good selectivity in wheat and corn, coupled with good general activity.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Test plants which had a height of 5 to 15 cm were sprayed with the preparation of the active compound in such a way as to apply the amounts of active compound per unit area which were prescribed. The concentration of the sprayed liquor was so chosen that the amounts of active compound were applied in 2,000 liters of water/ha. After three weeks, the degree of damage to the plants was rated in % damage in comparison to the development of the untreated control. The figures denoted:

0% = no action (like untreated control)
100% = total destruction

In this test the compounds (1), (3) and (5), for example, showed a very good selectivity in oats, wheat and maize, coupled with good general activity.

It will be understood that the specification and examples are illustrative but not limitative of the present invention and that other embodiments within the spirit and scope of the invention will suggest themselves to those skilled in the art.

We claim:

1. A 3-alken(in)yl-mercapto(amino)-4-amino-6-tert.-butyl-1,2,4-triazin-5-one of the formula

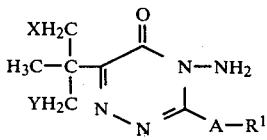

in which

A is sulphur or $-NR^2-$, $R^2$ is a hydrogen atom or an alkyl group having 1 to 4 carbon atoms, $R^1$ is an alkenyl or alkinyl group having 3 to 6 carbon atoms, X is a halogen atom or an alkoxy group having 1 to 4 carbon atoms, and Y is a hydrogen or halogen atom or an alkoxy group having 1 to 4 carbon atoms.

2. A compound according to claim 1, in which

X is a fluorine, chlorine or bromine atom or an alkoxy group having 1 to 4 carbon atoms, and Y is a hydrogen, fluorine, chlorine or bromine atom or an alkoxy group having 1 to 4 carbon atoms.

3. A compound according to claim 1, in which $R^2$ is a hydrogen atom or a methyl or ethyl group, $R^1$ is a radical selected from $-CH_2-CH=CH_2$, $-CH_2-CH=CH-CH_3$, $-CH_2-C(CH_3)=CH_2$, $-CH(CH_3)-CH=CH_2$, $-C(CH_3)_2-CH=CH_2$, $-CH_2C\equiv CH$, $-CH(CH_3)-C\equiv CH$ and $-C(CH_3)_2-C\equiv CH$, X is a fluorine or chlorine atom or a methoxy, ethoxy or isopropoxy group, and Y is a hydrogen, fluorine or chlorine atom or a methoxy, ethoxy or isopropoxy group.

4. A compound according to claim 1, wherein such compound is 4-amino-6-(chloro-tert.-butyl)-3-propargylthio-1,2,4-triazin-5-one of the formula

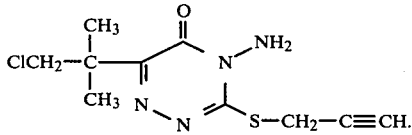

5. A compound according to claim 1, wherein such compound is 3-allylamino-4-amino-6-(fluoro-tert.-butyl)-1,2,4-triazin-5-one of the formula

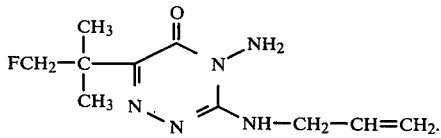

6. A compound according to claim 1, wherein such compound is 4-amino-6-(fluoro-tert.-butyl)-3-propargylthio-1,2,4-triazin-5-one of the formula

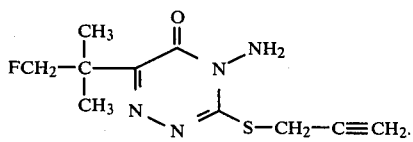

7. A compound according to claim 1, wherein such compound is 3-allylamino-4-amino-6-(chloro-tert.-butyl)-1,2,4-triazin-5-one of the formula

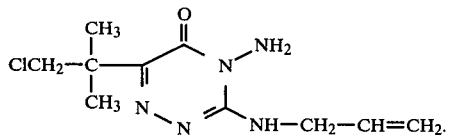

8. A herbicidal composition comprising a herbicidally effective amount of a compound according to claim 1 in admixture with a diluent.

9. A method combating weeds comprising applying to the weeds, or to a habitat thereof, a herbicidally effective amount of a compound according to claim 1.

10. The method according to claim 9, wherein such compound is
4-amino-6-(chloro-tert.-butyl)-3-propargylthio-1,2,4-triazin-5-one,
3-allylamino-4-amino-6-(fluoro-tert.-butyl)-1,2,4-triazin-5-one,
4-amino-6-(fluoro-tert.-butyl)-3-propargylthio-1,2,4-triazin-5-one or
3-allylamino-4-amino-6-(chloro-tert.-butyl)-1,2,4-triazin-5-one.

* * * * *